(12) United States Patent
Griffin et al.

(10) Patent No.: US 6,238,049 B1
(45) Date of Patent: May 29, 2001

(54) INTERACTIVE SELF-DIAGNOSTIC SYSTEM

(76) Inventors: Joanne Sawhill Griffin; Peter Burley Griffin, both of 1152 Center Dr., St. Louis, MO (US) 63117

(*) Notice: Subject to any disclaimer, the term of this patent is extended or adjusted under 35 U.S.C. 154(b) by 0 days.

(21) Appl. No.: 09/439,108

(22) Filed: Nov. 12, 1999

(51) Int. Cl.⁷ .......................................................... A61B 3/00

(52) U.S. Cl. ............................................................. 351/243

(58) Field of Search ..................................... 351/205, 223, 351/226, 237, 238, 239, 242, 243

(56) References Cited

U.S. PATENT DOCUMENTS

| | | |
|---|---|---|
| 416,599 | 12/1889 | Green . |
| 667,973 | 2/1901 | Cross . |
| 3,490,832 | 1/1970 | Mitsubishi et al. . |
| 3,808,354 | 4/1974 | Feezor et al. . |
| 3,891,311 | 6/1975 | Fletcher et al. . |
| 3,974,335 | 8/1976 | Blackledge . |
| 4,367,015 | 1/1983 | Waltuck et al. . |
| 4,869,589 | 9/1989 | Blair et al. . |
| 4,958,280 | 9/1990 | Pauly et al. . |
| 5,170,362 | 12/1992 | Greenberg et al. . |
| 5,191,367 * | 3/1993 | Salibello ............... 351/243 |
| 5,325,136 * | 6/1994 | Salibello ............... 351/243 |
| 5,436,681 | 7/1995 | Michaels . |
| 5,515,118 * | 5/1996 | Torrey et al. ......... 351/239 |
| 5,515,268 | 5/1996 | Yoda . |
| 5,589,897 | 12/1996 | Sinclair et al. . |

OTHER PUBLICATIONS http://www.rglasses.com/ichart.html, "Strength Chart for Reading Glasses from Reading Glasses International, Inc.", 1 p.

* cited by examiner

Primary Examiner—George Manuel
(74) Attorney, Agent, or Firm—Merchant & Gould P.C.

(57) ABSTRACT

A method of determining an eyeglass prescription for correcting a user's vision is provided. The method includes: prompting the user for selective parameters; configuring an eye chart for display based on the selective parameters; receiving sizing input from the user if the user increases or decreases the size of the eye chart until the eye chart appears clear; reconfiguring the eye chart based on the received sizing input; comparing the reconfigured eye chart to the configured eye chart; and determining the eyeglass prescription for correcting the user's vision based on a comparison between the reconfigured eye chart and the configured eye chart. A system for determining an eyeglass prescription for correcting a user's vision is also provided. The system includes a parameter module, a configure module, a receive module, a reconfigure module, a compare module, and a determine module. The parameter module prompts the user for selective parameters. The configure module configures the eye chart for display based on the selective parameters. The receive module receives sizing input from the user as the user increases or decreases the size of the eye chart until the eye chart appears clear. The reconfigure module reconfigures the eye chart based on the received sizing input. The compare module compares the reconfigured eye chart to the configured eye chart. The determine module determines the eyeglass prescription for correcting the user's vision based on comparison between the reconfigured eye chart and the configured eye chart.

20 Claims, 4 Drawing Sheets

INTERACTIVE SELF-DIAGNOSTIC SYSTEM

TECHNICAL FIELD

The present invention relates to software programs and more particularly to a software program for interactively self-diagnosing.

BACKGROUND OF THE INVENTION

Traditional eye exams are administered by an eye doctor. The patient looks at an eye chart on the wall in the doctor's office. The doctor places a series of different lenses between the patient's eyes and the eye chart. As the doctor changes the lenses back and forth, the patient provides verbal feedback to the doctor as to which lens is clearer. Once the appropriate lenses are determined by the doctor, the doctor places these lenses between the patient and the eye chart and asks the patient to read a particular line on the eye chart to verify the lenses are the correct lenses for the patient's particular vision. Upon verification, the doctor writes a prescription that the patient takes to an eyeglass retailer. The patient selects desirable frames and the retailer grinds the lens and inserts them into the frame or outsources the work of making the eyeglasses for the patient. These eye exams are relatively expensive and time consuming.

In some instances, different sized eye charts have been placed on the Internet with corresponding prescriptions to correct the user's vision based on which eye chart is most readable. These primitive charts have many disadvantages. For example, these eye charts do not account for any user parameter's, such as the user's monitor size, the user's monitor resolution, and how far away the user is sitting from the monitor. In addition, these charts are fixed in size and therefore allow limited flexibility in the diagnosis of the user's vision. Also, the ordering of eyeglasses does not allow for different prescriptions for each eye.

Therefore, improvements are desirable.

SUMMARY OF THE INVENTION

In one aspect of the present invention, a method of determining an eyeglass prescription for correcting a user's vision is disclosed. The method comprises prompting the user for selective parameters; configuring an eye chart for display based on the selective parameters; receiving sizing input from the user as the user increases or decreases the size of the eye chart until the eye chart appears clear; reconfiguring the eye chart based on the received sizing input; comparing the reconfigured eye charge to the configured eye chart; and determining the eyeglass prescription for correcting the user's vision based on the comparison between the reconfigured eye chart and the configured eye chart.

Another aspect of the present invention includes a system for determining an eyeglass prescription for correcting a user's vision. The system comprises a parameter module, a configure module, a receive module, a reconfigure module, a compare module, and a prescription module. The parameter module prompts the user for selective parameters. The configure module configures the eye chart for display based on the selective parameters. The receive module receives sizing input from the user as the user increases or decreases the size of the eye chart until the eye chart appears clear. The reconfigure module reconfigures the eye chart based on the received sizing input. The compare module compares the reconfigured eye chart to the configured eye chart. The prescription module determines the eyeglass prescription for correcting the user's vision based on comparison between the reconfigured eye chart and the configured eye chart.

Another aspect of the present invention includes a computer program storage medium readable by a computing system and coding computer program instructions for executing a computer process for determining an eyeglass prescription for correcting the user's vision. The computer process is analogous to the method described above.

In yet another aspect of the present invention, a computer readable signal embodying a carrier wave readable by a computing system and encoding a computer program instructions for executing a computer process for determining an eyeglass prescription for correcting a user's vision. The computer process is analogous to the method described above.

A more complete appreciation of the present invention and its scope may be obtained from the accompanying drawings, which are briefly described below, from the following detailed descriptions of presently preferred embodiments of the invention and from the appended claims.

DETAILED DESCRIPTION OF THE INVENTION

Various embodiments of the present invention, including a preferred embodiment, are described in detail with reference to the drawings wherein like reference numerals represent like parts and assemblies throughout the several figures. Reference to the described embodiments does not limit the scope of the invention, which is limited only by the scope of the appended claims.

In general terms, the present disclosure provides an interactive system and method for self-diagnosing. In particular, the present disclosure provides a system and method for determining the proper correction for eye vision. The system and method enable a user to easily self-diagnose her eye correction by enlarging or reducing the letters on an eye chart until the user can easily read the letters. Based on the size of the letters, the system and method determines the proper correction or eye glass prescription for the user.

Figure 1:
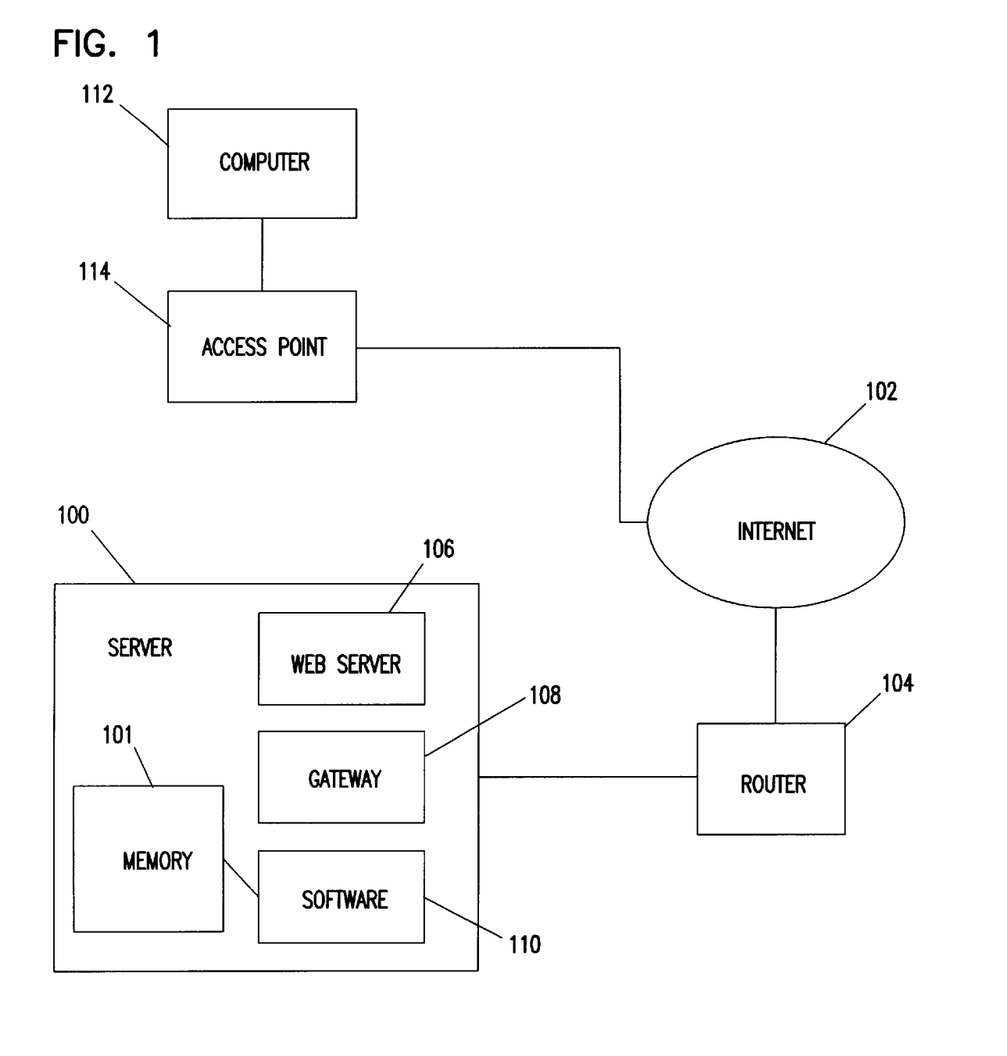
FIG. 1 is a schematic, block diagram representation of a networking system that embodies a self-diagnostic system, according to the present disclosure.

Attention is directed to FIG. 1. FIG. 1 is a schematic, functional diagram of a networking system that embodies the self-diagnostic eye exam system disclosed herein. In this example embodiment, the system is configured and arranged on an Internet system. In other example embodiments, the system could be configured and arranged in a number of different environments, for example on a stand-alone personal computer, such as a desktop personal computer; a handheld computer, such as a palm-size personal computer; a small computing device, such as a cellular phone; or on a client/server network.

Referring now to FIG. 1, the system is implemented on a server 100 that is connected, in either a wired or wireless environment, to the Internet 102. The Internet 102 is a vast collection of interconnected networks. Typically, a user accesses the Internet 102 through a computer 112, which contains client software. The computer 112 may be any computing device, for example, a personal computer, a handheld computer, a palm computer, or a small computing device, such as a cellular telephone. The client software is commonly a web browser. The user's computer 112 is typically connected to the Internet 102 through an Internet Service Provider (ISP). In this configuration, a user connects her computer 112 to an access point 114. The access point 114 provides access to the Internet 102, typically through an ISP using a modem. One type of format for displaying the information is in a web page that can be displayed on the user's computer 112.

Additionally, the server 100 is connected to the Internet 102 through a router 104, which provides a connection between networks. The router 104 filters addresses of information traveling over the Internet 102 and determines whether to accept that information or rout the information or instructions to a different destination. The server 100 includes memory 101, which can be either internal or external to the server 100 itself. The server 100 executes software including a web server 106, a common gateway interface 108, and one or more programs or software 110.

The web server 106 is the interface to the Internet 102 that allows text, graphics, commands, and other information to be transmitted and received over the Internet 102. The web server 106 provides the basis for a client/server configuration known as the World Wide Web. The common gateway interface 108 provides the set of rules that describe how the web server 106 communicates with other software 110 that is located on the server 100. The software 110 is the set of programs, routines, languages, and procedures used by the server 100 to perform particular functions and tasks. The software 110 accesses memory 101 to store and retrieve information.

Additionally, the server 100 can generate a web page that organizes information for display on the user's computer 112. The web page may also display links such as a hypertext link, which is an address for other information on the World Wide Web. When the user activates the link, the web browser or other client software on the user's computer 112 connects to the information, which might be another web page that is located at the specified address. The address might be for information accessed through the server 100 or might be for information accessed through an entirely different server that is also connected to the Internet 102. One type of link that can be used is a Uniform Resource Locator (URL).

Figure 2:
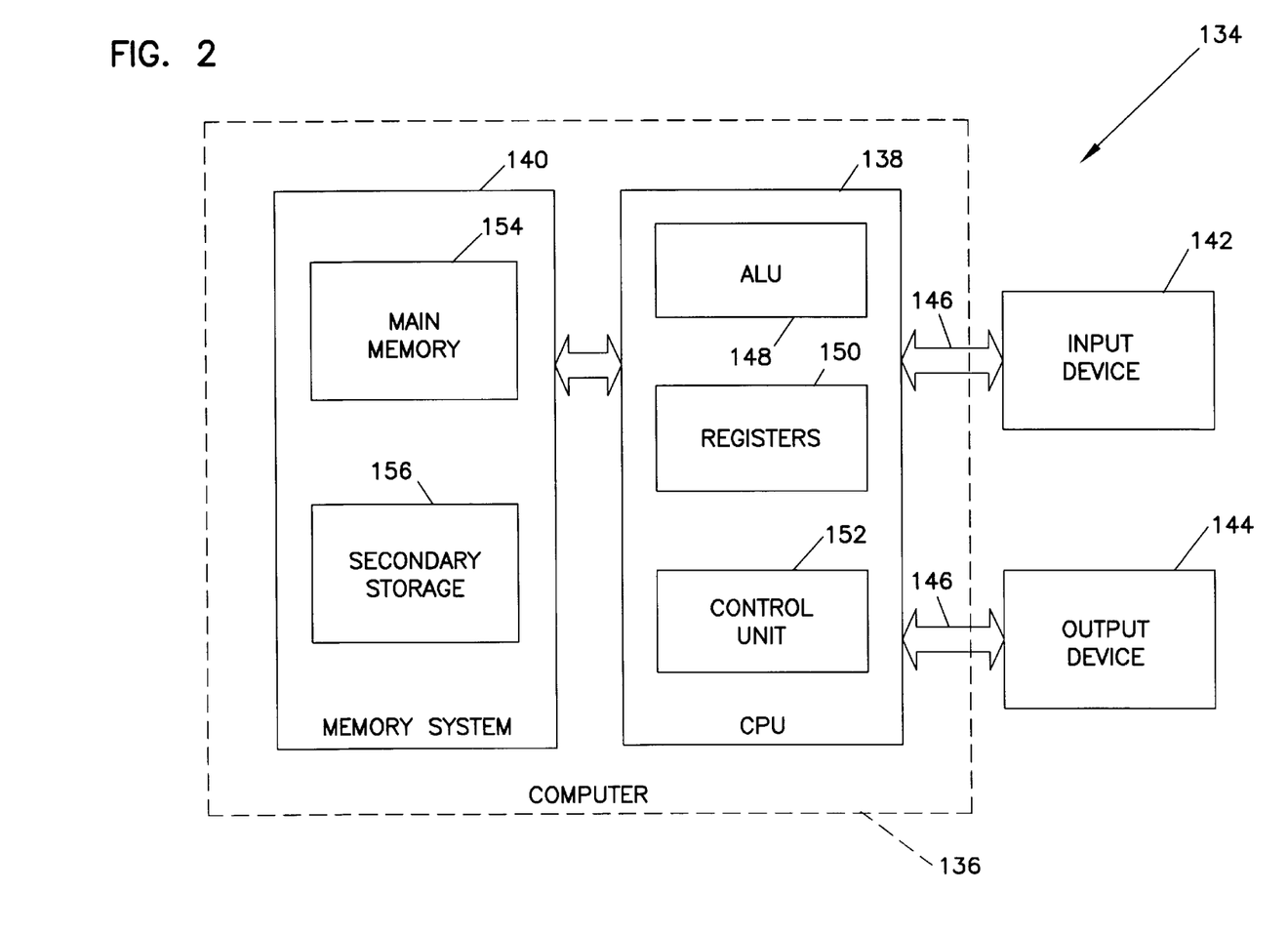
FIG. 2 is a schematic, block diagram representation showing a computing system that may be used to implement aspects of the present disclosure.

Attention is directed to FIG. 2. FIG. 2 is a schematic, block diagram representation showing a computing system that may be used to implement aspects of the present disclosure.

A computing system 134, or computer 136, incorporates a system 134 of resources for implementing an embodiment of the invention as shown in FIG. 2. The computing system 134 includes at least one central processing unit (CPU) 138, and a memory system 140. The memory system 140, an input device 142, and an output device 144 are coupled to the CPU by at least one system bus 146.

The CPU 138 is of conventional design and includes an Arithmetic Logic Unit (ALU) 148 for performing computations, a collection of registers 150 for temporary storage of data and instructions, and a control unit 152 for controlling operation of the system 134. The CPU 138 may be a microprocessor having any of a variety of architectures including, but not limited to, those architectures currently produced by Intel, Cyrix, AMD, IBM, and Motorola.

The memory system 140 includes a main memory 154, in the form of media such as random access memory (RAM) and read only memory (ROM), and may incorporate a secondary storage 156 in the form of long term storage mediums such as hard disks, floppy disks, tapes, compact disks (CDs), digital video disks (DVDs), flash memory, and the like and other devices that store data using electrical, magnetic, optical, or other recording media. The main memory 154 may also include video display memory, not shown, for displaying images through the output device 144, such as a display device, i.e., a monitor. The memory 140 can include any of a number of alternative components having a variety of storage capacities such as magnetic cassettes, memory cards, digital video disks, Bernoulli cartridges, random access memories, read only memories, and the like. Memory devices within the memory system 140 and their associated computer readable media provide non-volatile storage of computer readable instructions, data structures, programs, and other data for the computing system 134.

The system bus 146 may be any of several types of bus structures such as a memory bus, a peripheral bus, or a local bus using any of a variety of bus architectures.

The input device 142 can include a keyboard, a mouse, a microphone, a touch pad, a touch screen, or the like. The output device 144 can include a display, such as a computer monitor, a printer, a speaker, a touch screen, or the like. Some devices, such as a network interface or a modem, can be used as input or output devices 142 or 144. The input and output devices 142, 144 are connected to the computing system 134 through the system bus 146.

The computing system 134 further includes an operating system and usually one or more application programs. The operating system includes a set of programs that control the operation of the system 134, control the allocation of resources, provide a graphical user interface to the user and might also include accessory and utility programs. An application program is software that runs on top of the operating system software and uses computer resources made available through the operating system to perform application specific tasks desired by the users.

The server 100 can have configurations analogous to the computing system 134 configuration described above. Other configurations for the server can be used. Furthermore, the server can serve its own network or it can be dedicated to functioning as an Internet node. Other embodiments of the present invention can be implemented using systems and network configuration other than the Internet. Examples include Local Area Networks (LANs), Wide Area Networks (WANs), and Intranets. Yet other embodiments of the present invention can be implemented using client/server configurations other than the World Wide Web. The code for the system and method described herein can be embodied in any storage medium including hard drives, diskettes, CDs, DVDs, tapes, and the like.

In general terms, preferably, the logical operations of the various embodiments of the present invention are implemented as a sequence of computer implemented steps running on a computing system or as interconnected machine modules within the computing system. The implementation is a matter of choice dependent on the performance requirements of the computing system implementing the invention. Accordingly, the logical operations making up the embodiments of the present invention described herein are referred to alternatively as operations, steps, or modules.

Figure 3:
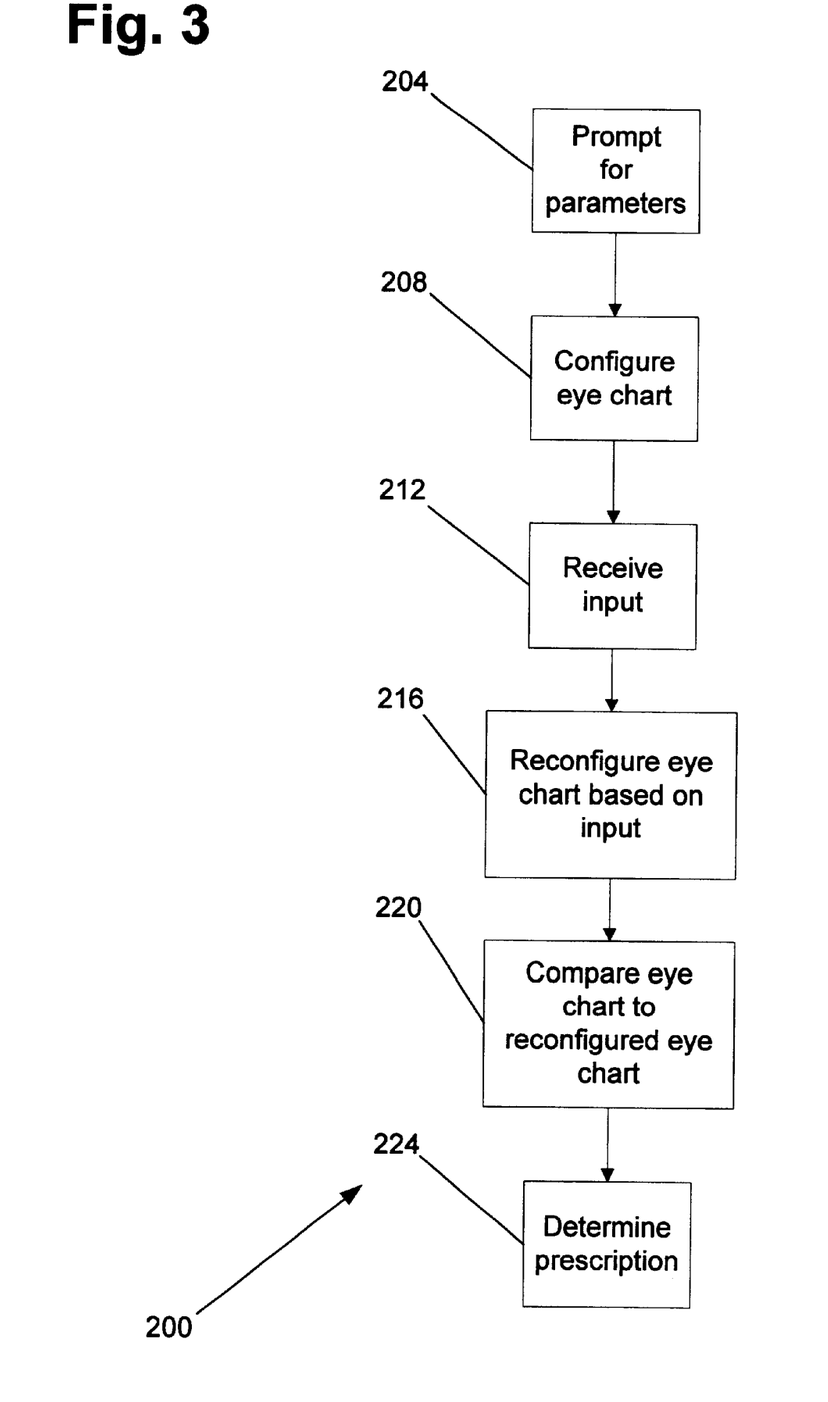
FIG. 3 is a schematic, block diagram depicting the basic functions of the self-diagnostic system, according to the present disclosure.

Attention is directed to FIG. 3. FIG. 3 is a preferred embodiment of the basic operations of a self-diagnostic eye exam system 200 according to the present disclosure. Generally, the user enters a World Wide Web page configured and arranged to implement an eye exam for a user. A parameter module 204 prompts for basic parameters about the user, for example, the distance the user is sitting from the display device of the user's computer. Based on these parameters, a configure module 208 configures the eye chart for the user. A receive module 212 receives input from the user, as the user adjusts the eye chart until she can read it clearly. A reconfigure module 216 reconfigures the eye chart based on the input received from the user. A compare module 220 compares the reconfigured eye chart to the original eye chart. A determine module 224 determines the proper prescription for the user's vision based on the parameters initially entered and based on information received from the compare module 220.

Figure 4:
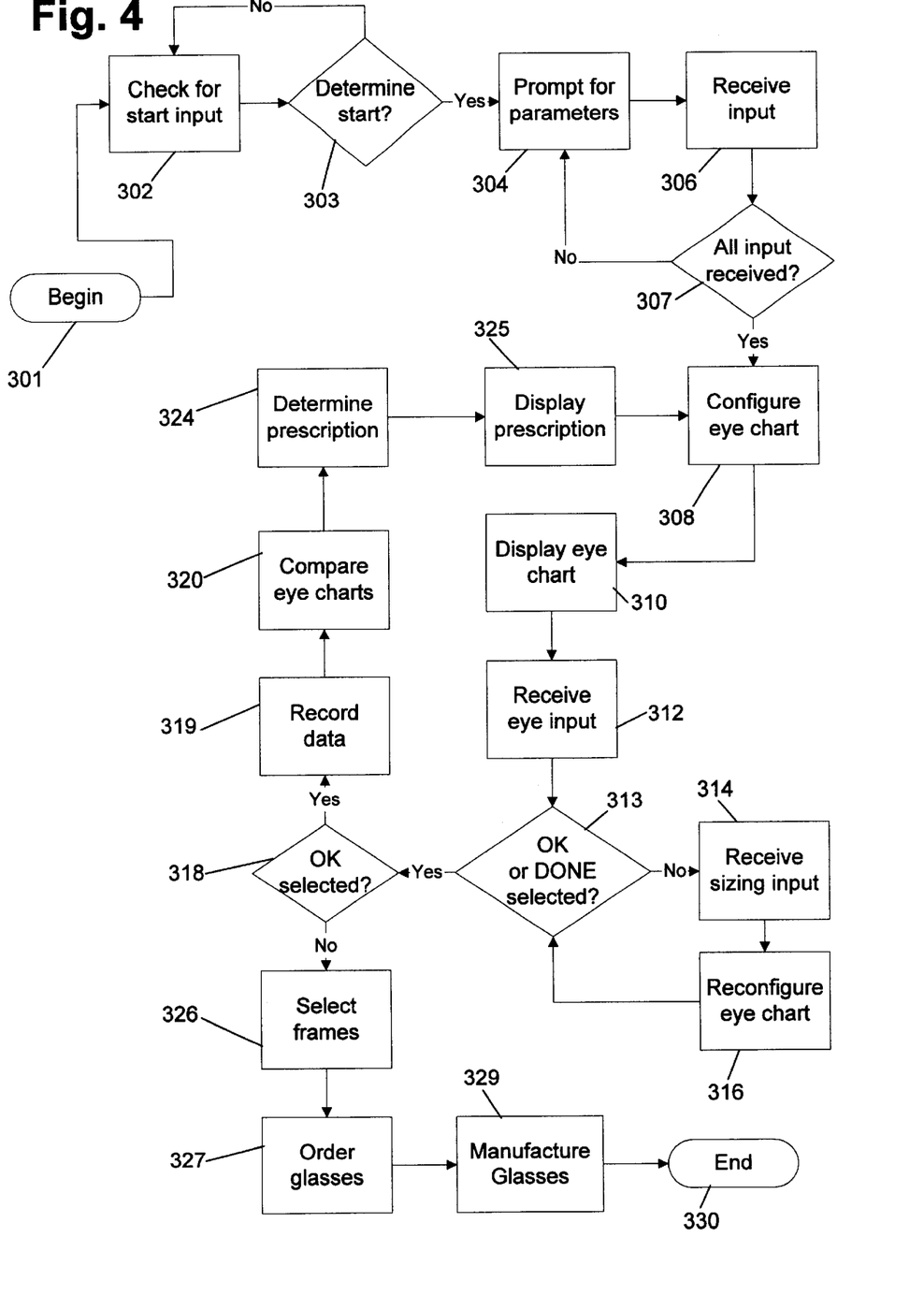
FIG. 4 is a flow chart representing logical operations of a self-diagnostic system, according to the present disclosure.

Attention is directed to FIG. 4. FIG. 4 is a flow chart representing logical operations of an eye exam system 300 for diagnosing a user's vision and proper correction. Entrance to the operational flow of the eye exam system 300 begins at a flow connection 301. A monitor module 302 checks for input from the user indicating the user's willingness to begin the eye exam. A check operation 303 determines if the user wishes to begin the eye exam. If the user does not wish to begin the eye exam, the operational flow branches "NO" to the monitor module 302. This process continues until the user wishes to begin the eye exam.

If the user wishes to begin the eye exam, the operational flow branches "YES" to a parameter module 304. The parameter module 304 prompts for specific input, for example, the user's monitor size, the distance the user is sitting from the monitor, and the resolution of the user's monitor. By the term "prompt," it is meant that the system 300 must determine certain information to administer the eye exam. In one example embodiment, the parameter module 304 asks the user a series of questions by displaying the questions on the user's computer monitor. In other example embodiments, the parameter module 304 might prompt the system 300 for these parameters. For example, the system 300 might include a distance measuring device, not shown, for measuring the distance the user is away from the user's computer monitor. In another example, the system 300 might be able to detect the size of the computer monitor to which it is connected. In another example embodiment, the system 300 might prompt the user for specific colors to be used in the display of information. This may be particularly helpful for users who have trouble seeing particular colors.

A receive module 306 receives the input in response to the prompts from the parameter module 304, either from the user, the system 300, or both. A check module 307 determines if all of the necessary input has been received. If not all of the necessary input has been received, the operational flow branches "NO" to the parameter module 304. The parameter module 304 continues to prompt for the needed input. When all of the necessary input has been received, the operational flow branches "YES" to a configure module 308.

The configure module 308 configures the eye chart according to the parameters received by the receive module 306. By the term "configures," it is meant the system 300 calibrates or sizes the eye chart based on the parameters received by the receive module 306. For example, because the eye chart might be displayed on a computer monitor, the size of the monitor and the distance the user is sitting from the monitor, in part, determine the size of the eye chart for use by the user. In one example embodiment, the configure module 308 appropriately sizes the eye chart for what should be 20/20 vision given the size of the monitor and the distance the user is away from the monitor. This resulting eye chart is the configured eye chart.

A display module 310 displays the configured eye chart on the display device, for example, the user's computer monitor, for the user to see. The display module 310 also provides instructions to the user for the administration of the eye exam. The instructions might include informing, for example, visually or audibly, the user to test only one eye at a time, for example, the left eye first and then the right eye, so that the system 300 can determine the proper correction for each eye. Another instruction might include informing the user to use an input device, such as a mouse, to increase or decrease the size of the eye chart until the eye chart is clearly in focus. Yet another instruction might include informing the user to select "DONE" when she believes the eye chart is clearly in focus.

A receive module 312 receives input from the user as to which eye is being tested, either the left or the right. Using the above example, the system 300 will test the left eye first and the right eye second. Of course, the right eye could be tested first or the left eye could be tested multiple times prior to starting the right eye test or any variation thereof. A done module 313 determines if the user has selected "OK" or "DONE." If the user has not selected "OK" or "DONE," the operational flow branches "NO" to a receive module 314. The receive module 314 receives input from the user to increase or decrease the size of the eye chart. A reconfigure module 316, reconfigures the eye chart based on the input received by the receive module 314. For example, the display module 310 might display a scroll bar across the bottom of the screen with an instruction to the user to use the scroll bar to increase or decrease the size of the eye chart until the eye chart is clear for the first eye. As the user uses an input device, such as a mouse, to move the scroll bar back and forth (or up and down), the receive module 314 receives the input from the user via the scroll bar. The reconfigure module 316 responds by reconfiguring the eye chart according to the input received by the receive module 314. In other words, the system, using the display device, acts as the lenses for the user. The resulting eye chart is the reconfigured eye chart. It should be noted that the eye chart might be reconfigured in discreet amounts, corresponding to normal corrective lens sizes, or the eye chart might be reconfigured on a continuous scale, allowing for very fine adjustments in the size of the eye chart.

Referring back to the done module 313, when the user believes the eye chart is clear for the eye being tested, the user will select "OK," and the operational flow branches "YES" to an OK module 318. The OK module 318 determines if the user selected "OK" or "DONE." If the user selected "OK," the operational flow branches "YES" to a record module 319. The record module 319 stores the data, or parameters, for the current size of the reconfigured eye chart in relation to its original size, or the size of the configured eye chart, determined by the configure module 308. A compare module 320 compares the reconfigured eye chart to the configured eye chart. A determine module 324 uses the data determined by the compare module 320 to determine the proper prescription for the user for the particular eye being tested. The determine module 324 will determine the proper correction for each eye based on the data stored by the record module 319 for each eye. A display module 325 will display the prescription on the display device for the particular eye tested. The operational flow proceeds to the configure module 308 where the system will reset the eye chart. The user might now re-test the same eye or test a different eye. Operational flow proceeds as described above.

Referring back to the OK module 318, if the user did not select "OK," and hence selected "DONE," the operational flow branches "NO" to a frame module 326. The frame module 326 allows the user to select the desired frames for her glasses. Preferably, the frame module 326 would provide a plurality of frames for the user to choose from. The frame module 326 might organize the plurality of frames to facilitate the user in choosing a particular frame. For example, the frame module 326 might organize the frames by manufacturer, price range, or by frame style. The user can then select from a group of frames corresponding to style or manufacturer. Preferably, the frame module 326 would also display the prices associated with each frame for the user.

Once the user has selected a particular frame, an order module 327 will take the user's order. Preferably, the order module 327 will compute the total price for the user, including the frame price and the price of the lenses. The order module 327 might also allow the user to add "options" to her lenses, i.e. anti-glare coating, and add clip-on sunglasses to the frames. The order module 327 would add on the appropriate price. The order module 327 would also inquire about shipping alternatives, delivery times, and take billing information. A manufacture module 329 will facilitate the manufacturing of the glasses to be shipped to the user using the prescription data from the determine module 324 and the frames selected by the user.

The operational flow ends at 330.

The operational flow chart depicted in FIG. 4 may best be understood in terms of an application example. A user accesses the eye exam system 300, for example, by entering a World Wide Web page that embodies the eye exam system 300. Of course, the eye exam system 300 could be distributed in other ways, for example, on a disk or CD. The user indicates she wishes to begin the eye exam, for example, by selecting "START." The check operation 303 determines the user is ready to begin the test. The parameter module 304 asks the user a series of questions, including how far the monitor is from the user, the size of the user's monitor, and the resolution of the monitor. The user responds, for example, by typing on her keyboard, that she is sitting 14 inches from her monitor, the monitor size is 17 inches diagonally, and the resolution of her monitor is 800×600. In an alternative embodiment, the parameter module 304 may provide a few choices and allow the user to choose the closest choice. For example, the parameter module 304 may give choices for a 15-inch, 17-inch, or 21-inch monitor. The user would check the closest size to her actual monitor.

The receive module 306 receives the responses from the user. The check module 307 ensures that all of the responses have been received by the receive module 306. When all of the necessary parameters have been received, the configure module 308 configures the eye chart for what a person who has 20/20 eyesight would see sitting 14-inches away from a 17-inch monitor having 800×600 resolution. The display module 310 displays the configured eye chart as configured by the configure module 308 and instructs the user how to use the system 300 to test her eyes. The user then selects the left eye to test first. The system 300 might provide two separate buttons, "left" and "right," for the user to click on to select. The receive module 312 receives the user's selection of the left eye.

If the user can clearly read the configured eye chart, the user selects "OK." If not, preferably, the user uses the scroll bar to increase or decrease the size of the eye chart until she can clearly read the eye chart. As the user increases or decreases the size of the eye chart, the receive module 314 receives the sizing input from the scroll bar. The reconfigure module 316 reconfigures the eye chart based on the sizing input received by the receive module 314. Thus, the user sees the eye chart increasing in size or decreasing in size as the user moves the scroll bar. This continues until the user selects "OK" or "DONE." The user will select "OK" when the eye chart can be clearly read.

If the user selected "OK," the OK module 318 branches "YES" to the record module 319. The record module records the reconfigured eye chart's size. The compare module 320 compares the recently used eye chart to the configured eye chart for the left eye. The determine module 324 uses information from the compare module 320 to determine the proper correction for the left eye. The display module 325 displays the prescription for the left eye on the output device. The operational flow proceeds to the configure module 308. The configure model 308 resets the eye chart back to the configured eye chart.

This time, the user selects the right eye and the selection is received by the receive module 312. It should be noted that the user could have selected the left eye again and proceeded as described above. The user may reselect the same eye to retest and reconfigure the prescription for that eye. The user may select the same eye as many times as she likes.

If the user can clearly read the configured eye chart, the user selects "OK." If not, preferably, the user uses the scroll bar to increase or decrease the size of the eye chart until she can clearly read the eye chart. As the user increases or decreases the size of the eye chart, the receive module 314 receives the sizing inputs from the scroll bar. The reconfigure module 316 reconfigures the eye chart based on the sizing input received by the receive module 314. Thus, the user sees the eye chart increasing in size or decreasing in size as the user moves the scroll bar. This continues until the user selects "OK" or "DONE." The user will select "OK" when the eye chart is clear.

If the user selected "OK," the OK module 318 branches "YES" to the record module 319. The record module records the reconfigured eye chart's size. The compare module 320 compares the reconfigured eye chart to the configured eye chart for the right eye. The determine module 324 uses the information from the compare module 321 to determine the proper correction for the right eye. The display module 325 displays the prescription for the right eye on the output device. The operational flow proceeds to the configure module 308. The configure module 308 resets the eye chart back to the configured eye chart.

At this point, the user sees her prescription displayed for each eye individually, as each eye might have different prescriptions. When the user has completed both eyes and is satisfied with the displayed prescriptions, the user selects "DONE" and operational flow branches to the frame module 326. The user selects a pair of frames for her glasses. The order module 327 takes the user's order based on the frame selection from the frame module 326. The manufacture module 329 facilitates the manufacture of the user's eyeglasses by using the frame selection received from the frame module 326 and the user's prescription for each eye received from the determine module 324.

In alternative embodiments, the principles described herein may be applied to a variety of different applications involving interactive, self-diagnosis. For example, the principles described herein may be applied to test a user's hearing by allowing a user to increase or decrease the volume of different pitched sounds until the user can clearly hear the sound. In another example, the principles described herein may be applied to shopping environments. The user could change the color of bananas. Based on the color, the system can determine the corresponding ripeness of bananas that the user wishes to order.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. A method of determining an eye glass prescription for correcting a user's vision, the method comprising:
   (a) prompting for selective parameters;
   (b) configuring a configurable eye chart based on the selective parameters;
   (c) receiving sizing input from the user as the user increases or decreases a size of the eye chart until the eye chart is configured to appear clear;
   (d) reconfiguring the eye chart, resulting in a reconfigured eye chart, based on the received sizing input;
   (e) comparing the reconfigured eye chart to the configured eye chart; and
   (f) determining the eye glass prescription for correcting the user's vision based on the comparison between the reconfigured eye chart and the configured eye chart.

2. A method according to claim 1 further comprising:
   (a) after said step of configuring, displaying the eye chart on a display device for the user.

3. A method according to claim 1 further comprising:
   (a) receiving input from the user regarding which eye is being tested.

4. A method according to claim 1 further comprising:
   (a) after said step of determining the eye glass prescription, displaying the eye glass prescription on a display device.

5. A method according to claim 4 wherein:
   (a) said step of displaying the eye glass prescription includes displaying the eye glass prescription for each individual eye on the display device.

6. A method according to claim 1 further comprising:
   (a) after said step of reconfiguring the eye chart, recording data associated with the eye chart and the reconfigured eye chart for later retrieval.

7. A method according to claim 1 wherein:
   (a) said step of prompting includes prompting for a display devices size, a monitor's resolution, or a distance.

8. A method according to claim 1 wherein:
   (b) said step of receiving includes receiving sizing input from the user as the user uses a scroll bar to increase or decrease the size of the eye chart until the eye chart is configured to appear clear.

9. A system for determining an eye glass prescription for correcting a user's vision, the system comprising:
   (a) a parameter module for prompting for selective parameters;
   (b) a configure module for configuring a configurable eye chart based on the selective parameters;
   (c) a first receive module for receiving sizing input from the user as the user increases or decreases the size of the eye chart until the eye chart appears clear;
   (d) a reconfigure module for reconfiguring the configured eye chart, resulting in a reconfigured eye chart, based on the received sizing input;
   (e) a compare module for comparing the reconfigured eye chart to the configured eye chart; and
   (f) a determine module for determining the eye glass prescription for correcting the user's vision based on the comparison between the reconfigured eye chart and the configured eye chart.

10. A system according to claim 9, further comprising:
    (a) a display module for displaying the eye chart on a display device for the user.

11. A system according to claim 9, further comprising:
    (a) a second receive module for receiving input from the user regarding which eye is being tested.

12. A system according to claim 9, further comprising:
    (a) a display module for displaying the eye glass prescription on a display device.

13. A system according to claim 9, further comprising:
    (a) a record module for recording data associated with the eye chart and the reconfigured eye chart for later retrieval.

14. A computer program storage medium readable by a computing system and encoding a computer program of instructions for executing a computer process for determining an eye glass prescription for correcting a user's vision, the computer process comprising:
    (a) prompting for selective parameters;
    (b) configuring a configurable eye chart based on the selective parameters;
    (c) receiving sizing input from the user as the user increases or decreases a size of the eye chart until the eye chart is configured to appear clear;
    (d) reconfiguring the eye chart, resulting in a reconfigured eye chart, based on the received sizing input;
    (e) comparing the reconfigured eye chart to the configured eye chart; and
    (f) determining the eye glass prescription for correcting the user's vision based on the comparison between the reconfigured eye chart and the configured eye chart.

15. A computer process according to claim 14 further comprising:
    (a) after said step of configuring, displaying the eye chart on a display device for the user.

16. A computer process according to claim 14 further comprising:
    (a) receiving input from the user regarding which eye is being tested.

17. A computer process according to claim 14 further comprising:
    (a) after said step of determining the eye glass prescription, displaying the eye glass prescription on a display device.

18. A computer data signal embodied in a carrier wave readable by a computing system and encoding a computer program of instructions for executing a computer process for determining an eye glass prescription for correcting a user's vision, the computer process comprising:
    (a) prompting for selective parameters;

(b) configuring a configurable eye chart based on the selective parameters;

(c) receiving sizing input from the user as the user increases or decreases a size of the eye chart until the eye chart is configured to appear clear;

(d) reconfiguring the eye chart, resulting in a reconfigured eye chart, based on the received sizing input;

(e) comparing the reconfigured eye chart to the configured eye chart; and (f) determining the eye glass prescription for correcting the user's vision based on the comparison between the reconfigured eye chart and the configured eye chart.

19. A computer process according to claim 18 further comprising:

(a) after said step of configuring, displaying the eye chart on a display device for the user.

20. A computer process according to claim 18 further comprising:

(a) after said step of determining the eye glass prescription, displaying the eye glass prescription on a display device.

* * * * *